(12) United States Patent
Aravanis et al.

(10) Patent No.: US 6,929,945 B2
(45) Date of Patent: Aug. 16, 2005

(54) MALE FERTILITY ASSAY METHOD AND DEVICE

(75) Inventors: Alexander M. Aravanis, Palo Alto, CA (US); Jason L. Pyle, Palo Alto, CA (US)

(73) Assignee: Advanced Fluidix Laboratories LLC, Incline Village, NV (US)

(*) Notice: Subject to any disclaimer, the term of this patent is extended or adjusted under 35 U.S.C. 154(b) by 0 days.

(21) Appl. No.: 10/705,162

(22) Filed: Nov. 6, 2003

(65) Prior Publication Data

US 2004/0146850 A1 Jul. 29, 2004

Related U.S. Application Data

(60) Provisional application No. 60/511,798, filed on Oct. 16, 2003, and provisional application No. 60/431,872, filed on Dec. 9, 2002.

(51) Int. Cl.[7] ................................................ C12M 1/34
(52) U.S. Cl. ................................ 435/288.5; 435/288.7; 435/808; 422/82.05; 422/82.09
(58) Field of Search .......................... 435/288.1, 288.4, 435/288.7, 305.2, 309.1, 808; 422/100, 102, 82.05, 82.09; 359/29.39, 343, 246, 440–442, 398; 250/328, 428, 461.2; 73/864.11

(56) References Cited

U.S. PATENT DOCUMENTS

| | | |
|---|---|---|
| 5,116,125 A | 5/1992 | Rigler |
| 5,296,375 A | 3/1994 | Kricka et al. |
| 5,427,946 A | 6/1995 | Kricka et al. |
| 5,466,587 A | 11/1995 | Fitzpatrick-McElligott et al. |
| 5,492,674 A | 2/1996 | Meserol |
| 5,580,794 A | 12/1996 | Allen |
| 5,744,366 A | 4/1998 | Kricka et al. |
| 5,837,546 A | 11/1998 | Allen et al. |
| 5,849,713 A | 12/1998 | Eisenbach |
| 5,935,800 A | 8/1999 | Alvarez |
| 2002/0019060 A1 | 2/2002 | Petersen et al. |
| 2002/0025576 A1 | 2/2002 | Nortrup et al. |
| 2002/0133306 A1 | 9/2002 | Wilkinson et al. |
| 2003/0129671 A1 | 7/2003 | Wilding et al. |
| 2003/0162304 A1 | 8/2003 | Dority et al. |
| 2003/0165812 A1 | 9/2003 | Takayama et al. |

FOREIGN PATENT DOCUMENTS

| | | |
|---|---|---|
| EP | 0439893 A2 | 8/1991 |
| WO | WO 01/41736 A2 | 6/2001 |
| WO | WO 01/60968 A1 | 8/2001 |
| WO | WO 03/072765 A1 | 9/2003 |

OTHER PUBLICATIONS

Copy of International Search Report from PCT Application No. PCT/US03/39069.

Kricka, L. J. et al., "Micromachined analytical devices: microchips for semen testing[1]", *Journal of Pharmaceutical and Biomedical Analysis*, 15:1443–1447, 1997.

Primary Examiner—David Redding
(74) Attorney, Agent, or Firm—Peter J. Dehlinger; Perkins Coie LLP

(57) ABSTRACT

A method and device for assaying sperm motility in a forward direction and density of active sperm in a semen sample are disclosed. The device includes a microfluidics structure having a sample reservoir, a downstream collection region and a microchannel extending therebetween. The microchannel is dimensioned to confine sample sperm to single-direction movement within the channel, such that sperm in a semen sample placed in the sample reservoir enter and migrate along the microchannel toward and into the collection region. Also included is a detector for detecting the presence of labeled sperm in the microchannel or collection region, and an electronics unit operatively connected to the detector for (i) receiving detector signals, (ii) based on the detector signals received, determining sperm motility and density in the sperm sample, and (iii) displaying information related to sperm motility and density.

14 Claims, 11 Drawing Sheets

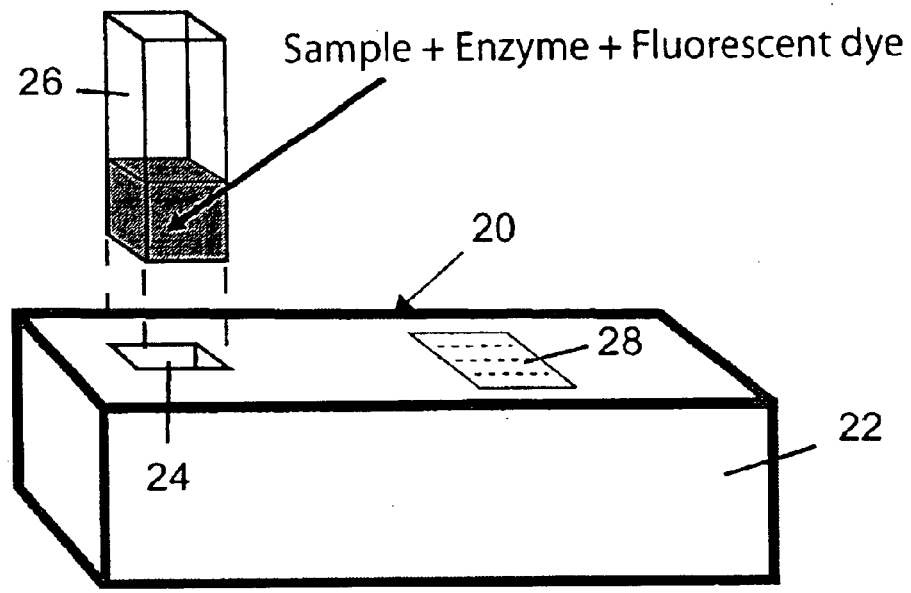
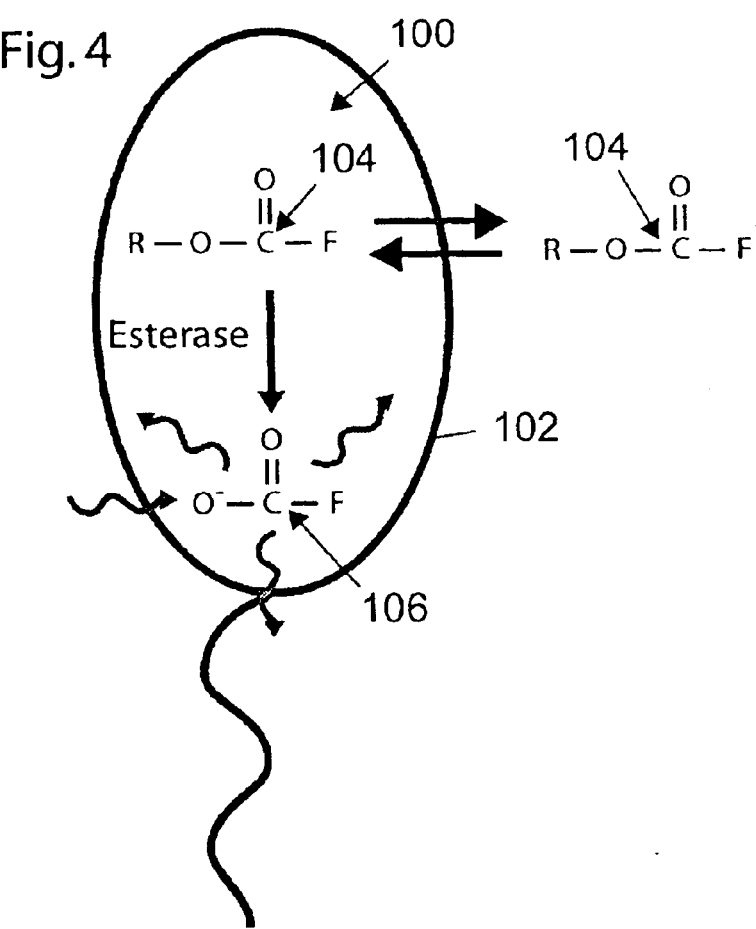

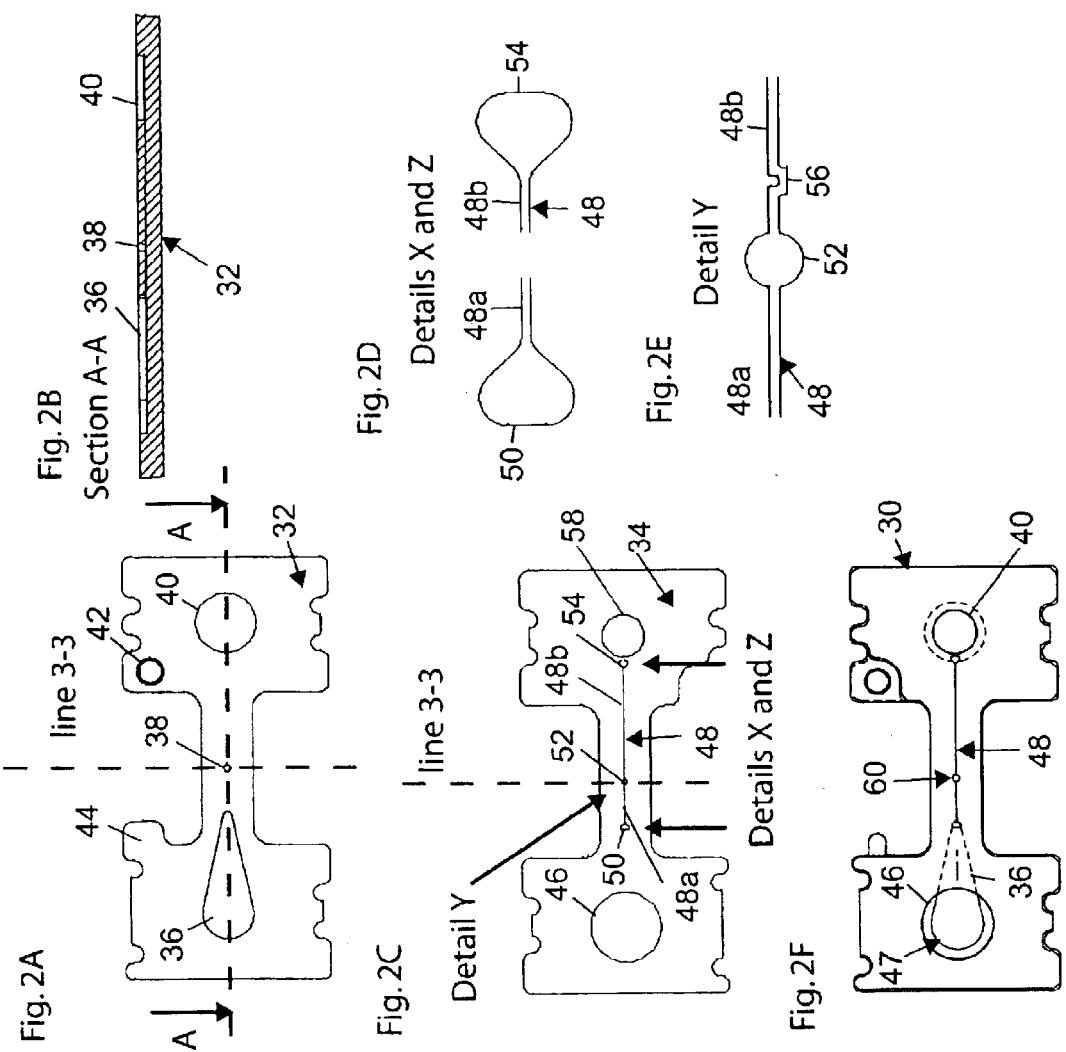

Xsection line 3-3

Microfludic part

Microfludic collecting chamber

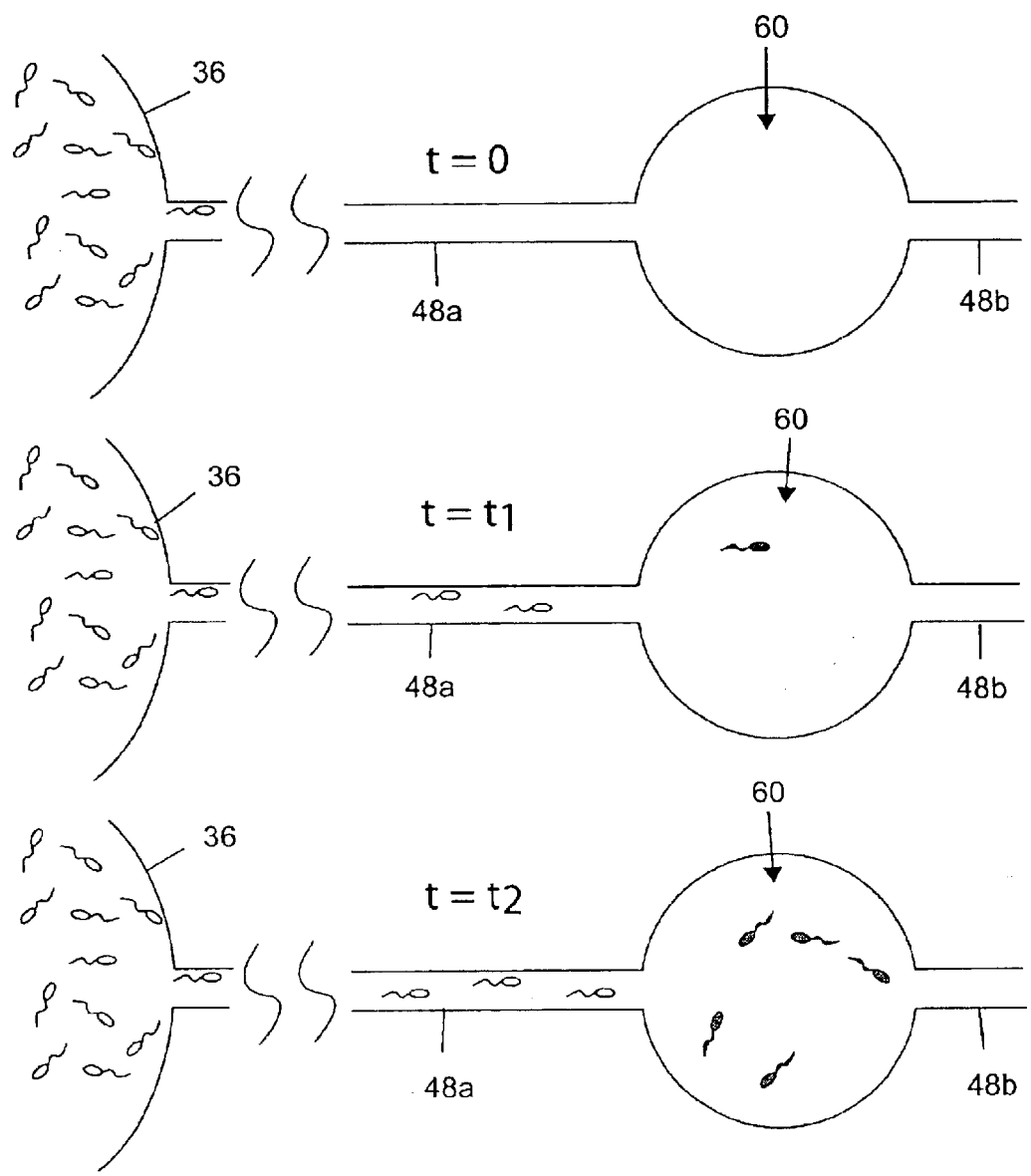
Fig. 5A-C

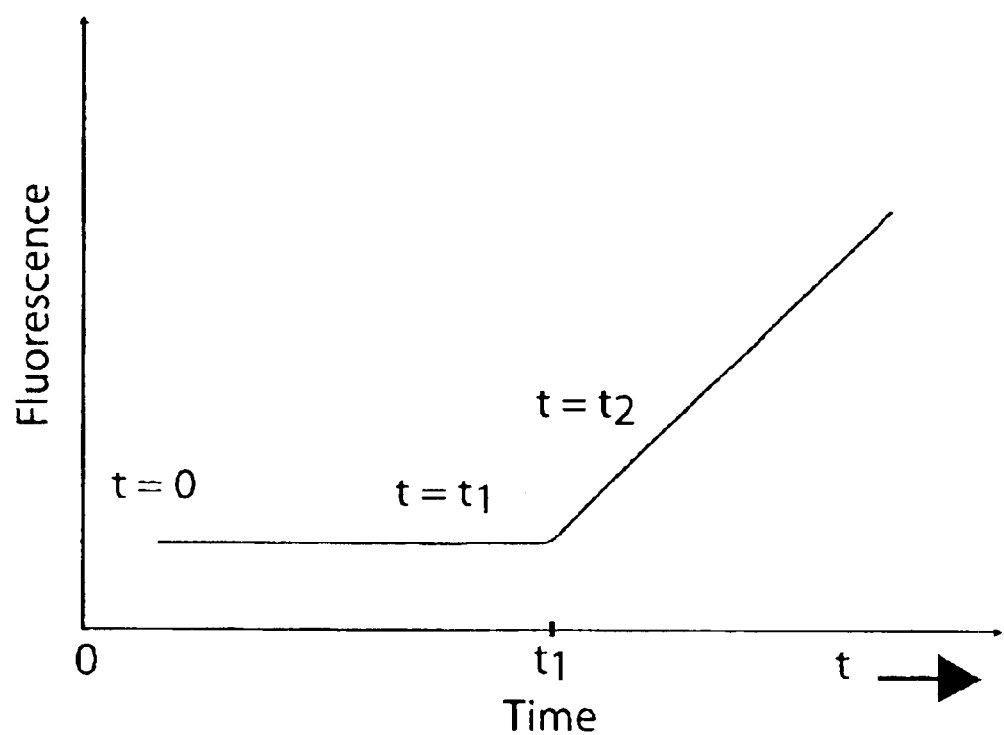

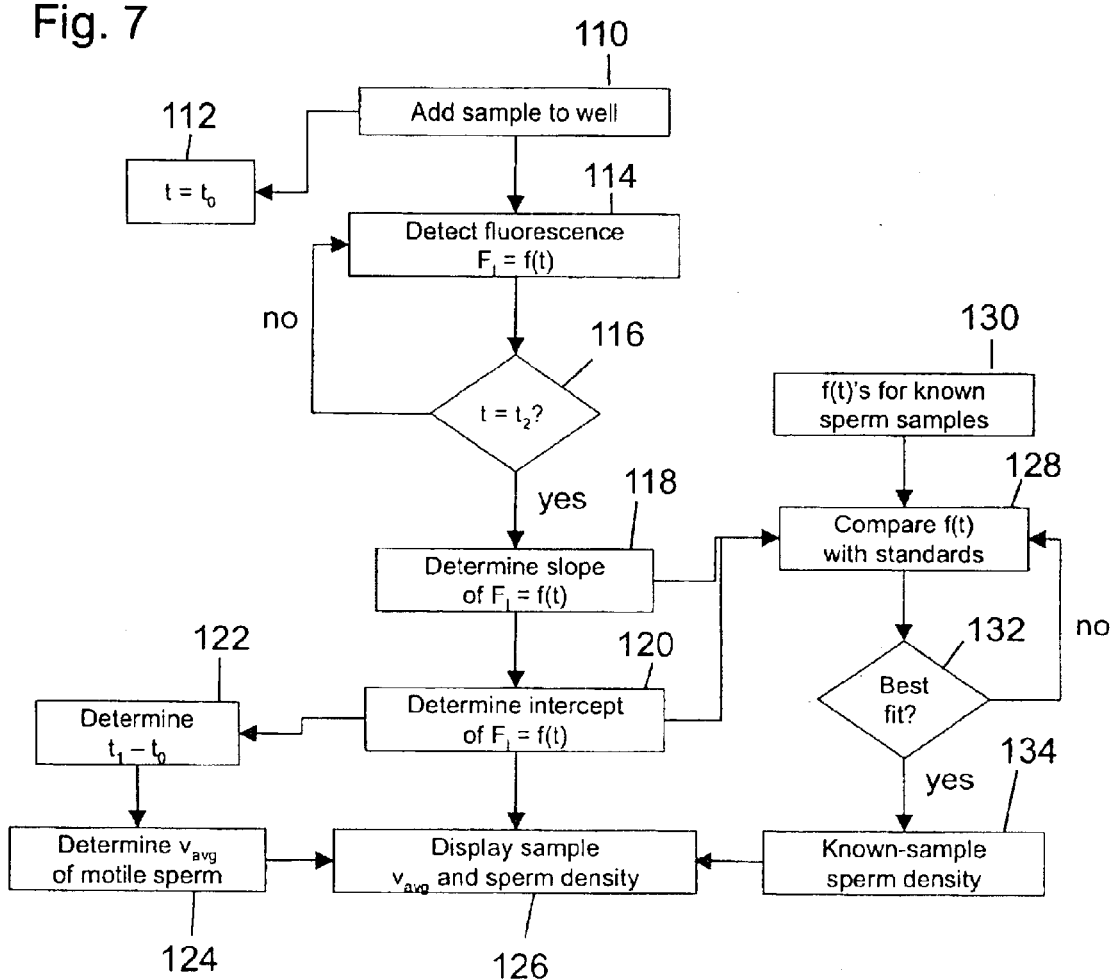

Electrical frequency response = Impedance, $Z(f) = \dfrac{V}{I(f)}$, for all f

Fig. 12A    Simple LED display
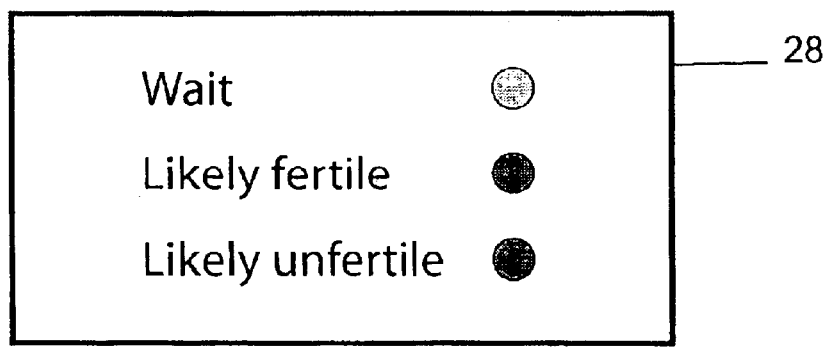
Fig. 12B    Quantitative LCD display
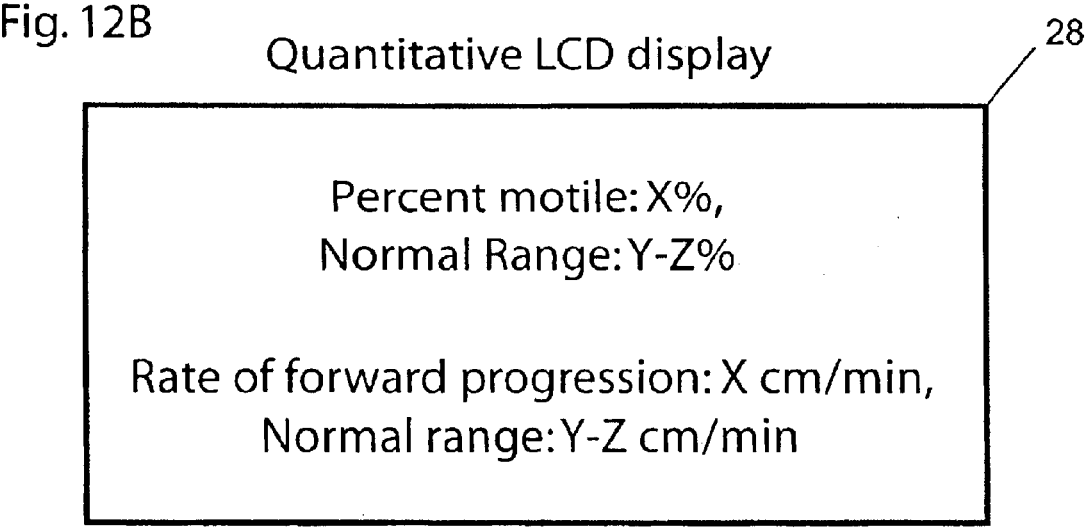

US 6,929,945 B2

MALE FERTILITY ASSAY METHOD AND DEVICE

This application claims the priority of U.S. Ser. No. 60/511,798 filed on Oct. 16, 2003, and U.S. Ser. No. 60/431,872 filed on Dec. 9, 2002, both of which are incorporated in their entirety herein by reference.

FIELD OF THE INVENTION

The present invention relates to a method and device for assaying male fertility, and in particular, to a method and device for determining sperm motility in a forward direction, and the density of active sperm.

BACKGROUND OF THE INVENTION

Couples in the United States and the other industrialized countries have between a 15–20% likelihood of failing to conceive children without some medical intervention. Male Factor Infertility is directly responsible for approximately one-third and a contributing factor in over half of failed conceptions. In order to plan the most appropriate medical interventions, the status of the male semen sample must be accurately determined. According to the World Health Organization criteria for male fertility, the primary factors governing male fertility are semen volume, and sperm cell density, motility, forward progression, and morphology. These criteria are not independent. For example, a semen sample with a high-density of forwardly progressing sperm also has high motility and an acceptably low rate of morphological defects. Therefore, by correctly measuring the density of forwardly progressing sperm cells within a semen sample and comparing these results to international medical standards, Male Factor Infertility can be ruled-out as a cause for failed conception, or identified and treated according to current medical practices.

Currently, nearly all semen samples are analyzed in the laboratory setting at major hospitals, medical centers, and fertility clinics secondary to a physician referral. A trained technician performs most semen analysis. The sample is observed under a microscope and several aspects of the sperm cell composition are quantified, such as density, percent motility, percent morphologically abnormal, and forward progression. At this time, a single over-the-counter product that performs semen cell count is also available in the UK and US.

Analysis of semen samples for couples who are failing to conceive is currently limited by several factors. Many couples are reluctant to seek medical advice for fertility problems until difficulties and stressors have persisted for long periods of time. Once medical advice is sought, men are particularly unwilling to seek semen analysis due to embarrassment and lack of privacy. The need for trained personnel and laboratory testing is partly responsible for the high cost of fertility management. Low cost and private alternatives to semen analysis, such as the in-home cell count assay available from the UK, fail to discriminate between sperm cells in the semen sample and other cell types and fail to analyze any motility characteristics of the sperm cells within the sample. It would thus be desirable to provide an in-home method and device for assaying sperm count and motility that substantially overcomes these limitations.

SUMMARY OF THE INVENTION

In one aspect, the invention includes a method for assaying sperm motility in a forward direction and density of active sperm in a semen sample. In practicing the method, a semen sample is placed in a sample reservoir, and allowed to migrate from the sample reservoir into and along a microchannel that confines the sperm to single-direction movement within the channel toward a downstream collection region. The sperm sample characteristics are determined by measuring the rate of migration and the flux of sperm through the microchannel. The microchannel has preferred width and depth dimensions each in the range of 10 to 100 $\mu$m.

In one general embodiment, the microchannel has a known length, the downstream collection region includes a collection reservoir with a known volume, and the step of measuring the rate of migration and the flux of sperm through the microchannel may include the steps of: (1) measuring the change in concentration of cells present in the collection reservoir as a function of time, (2) determining from step (1), and the volume of the collection reservoir, the density of active sperm in the sample as a function of time, and (3) determining from step (1), the average rate of migration of sperm through the microchannel in a downstream direction. More specifically, step (1) may include generating a time-dependent function whose slope approximates the change in number of cells present in the collection reservoir per unit of time, and whose intercept present in the collection reservoir per unit of time, and whose intercept approximates the time to first appearance of sperm in the collection reservoir, step (2) may include comparing the function with one or more standard functions generated with semen samples of different known sperm counts and rates of forward progression, and step (3) may include determining from this intercept, the average rate of travel in a forward direction of the sperm.

In this embodiment, the sperm in the sample may be labeled with a fluorescent reporter, and step (1) may include measuring fluorescence emission in the collection reservoir. This labeling may include exposing sperm to a fluorescence reporter having a cleavable ester group that promotes uptake of the reporter into sperm in an uncharged state, and inhibits efflux of the reporter from sperm in a charged, cleaved-ester state.

In another general embodiment, the width of the microchannel is such as to limit sperm movement along the microchannel to single file, and the step of measuring the rate of migration and the flux of sperm through the microchannel may include the steps of (1) detecting individual sperm as they migrate past a detection zone in the microchannel, in an upstream to downstream direction, (2) counting the number of sperm that migrate past the detection zone, and (3), determining the rate of migration of individual sperm through the detection zone.

The width of the detection zone in this embodiment is preferably between about 15–40 $\mu$m. The detection zone may be defined by a pair of adjacent, axially spaced detectors, and step (1) may include correlating signals received from each detector to enhance the signal-to-noise ratio for each detection event. Alternatively, where the detection zone is defined by a pair of adjacent, axially spaced detectors, and step (3) may additionally include using the time interval between signals received from the detectors to determine the rate of migration of sperm within the microchannel.

The sperm in the sample may be labeled with a fluorescent reporter, and step (1) may include measuring the fluorescence of sperm migration through the detection zone. As above, the sperm may be labeled with a fluorescence reporter having a cleavable ester group that allows uptake of the reporter into sperm in a substantially uncharged state, but inhibits efflux of the reporter from sperm in a charged, cleaved-ester state.

Alternatively, sperm in the sample may be labeled with a magnetic or conductive-metal particles, and step (1) may include measuring an electrical signal (i) generated by a circuit element placed adjacent the detection zone, and (ii) characteristic of a sperm labeled with magnetic or conductive-metal particles passing through the detection zone. Step (3) may include determining the rate of migration of a sperm passing through the detection zone from the rate of change of signal characteristics generated by the circuit element.

In another aspect, the invention includes a device for assaying sperm motility and density of motile sperm in a semen sample. The device includes a microfluidics structure having a sample reservoir, a downstream collection region and a microchannel extending therebetween. The microchannel is dimensioned to confine sample sperm to single-direction movement within the channel, such that sperm in a semen sample placed in the sample reservoir enter and migrate along the microchannel toward and into the collection region. Also included is a detector for detecting the presence of labeled sperm in the microchannel or collection region. An electronics unit in the device is operatively connected to the detector for (i) receiving detector signals, (ii) based on the detector signals received, determining sperm motility and density in the sperm sample, and (iii) displaying information related to sperm motility and density.

The device may be formed as a self-contained unit, e.g., a disposal unit, with its own power supply (battery) for powering the control unit and detector. The microchannel in the device has preferred width and depth dimensions each in the range of 10–100 $\mu$m.

In one general embodiment, the microchannel has a known length, the downstream collection region includes a collection reservoir with a known volume, and the electronics unit operates to (1) measure the change in concentration of cells present in the collection reservoir as a function of time, (2) determine from step (1), and the volume of the collection reservoir, the density of active sperm in the sample as a function of time, and (3) determine from step (1), the average rate of migration of sperm through the microchannel in a downstream direction. More specifically, the electronics unit may operate, in carrying out step (1), to generate a time-dependent function whose slope approximates the change in number of cells present in the collection reservoir per unit of time, and whose intercept approximates the time to first appearance of sperm in the collection reservoir, in carrying out step (2) to compare the function with one or more standard functions generated with semen samples of different known sperm counts and rates of forward progression, and in carrying out step (3) to determine from the intercept, the average rate of travel in a forward direction of the sperm.

In this embodiment, the detector may include an LED, first and second photodetectors, and a unitary optical member designed to (1) direct light from the LED to the first photodetector, (2) direct light from the LED through the collection reservoir, and (3) direct emitted fluorescence from the collection reservoir capture to the second photodetector. The optical member may be a unitary member composed of a plurality of optical elements having different indices of refraction.

In another general embodiment, the detector is disposed adjacent a detection zone in the microchannel. In this embodiment, the electronics unit may operate to (1) detect individual sperm as they migrate through the zone in the microchannel, in an upstream to downstream direction, (2) count the number of sperm that migrate through the detection zone, and (3) determine the rate of migration of individual sperm through the detection zone. In this embodiment, the width of the microchannel is preferably between about 15–40 $\mu$m.

The detection zone may be defined by a pair of adjacent, axially spaced detectors, and step (1) may include correlating signals received from each detector to enhance the signal-to-noise ratio for each detection event. Alternatively, where the detection zone is defined by a pair of adjacent, axially spaced detectors, and step (3) may additionally include using the time interval between signals received from the detectors to determine the rate of migration of sperm within the microchannel. The detector(s) may be fluorescent detectors.

Alternatively, the detector may include a circuit element disposed adjacent the detection zone, where the circuit element is responsive to nearby movement of magnetic- or metal-conductor particles, such that movement of sperm labeled with magnetic or metal-conductor particles through the detection zone in the microchannel will alter the inductance of the element. The electronics unit in this embodiment may include a detector circuit operatively coupled to the element for detecting changes in the inductance of the element. The electronics unit may operate, in carrying out step (3), to determine the rate of migration of a sperm passing through the detection zone from the rate of change of signal characteristics generated by the circuit element.

The sample-receiving reservoir in the device may communicate with the upstream end of the microchannel through a degradable, liquid-impervious plug, and the reservoir contains an enzyme capable of degrading said plug.

These and other objects and features of the invention will become more fully apparent when the following detailed description of the invention is read in conjunction with the accompanying drawings.

BRIEF DESCRIPTION OF THE DRAWINGS

FIG. 1 shows, in perspective view, an assay device constructed according to one embodiment of the invention;

FIGS. 2A–2F show (2A) a plan view of the bottom plate in a microfluidics assembly constructed in accordance with the invention, (2B) a sectional view through line A—A in FIG. 2A showing a central detection reservoir and wells for connecting the input ports to the microchannel, (2C), a plan view of the top plate in the microfluidics assembly, (2D), detail of end regions of a microfluidics channel and opposing reservoirs formed in the top plate; and (2E) detail of microfluidic channel and reservoir outline formed in the top plate; and (2F) the full assembly with the top and bottom plates stacked;

FIG. 4 illustrates labeling of sample sperm with ester-linked fluorescent reporter;

FIGS. 5A–5C illustrate conditions of sample movement and distribution during operation of the device in FIG. 1, at three different time points;

FIG. 6 shows a typical sperm-concentration function generated by the device of FIG. 1 during an assay operation;

FIG. 7 is a flow diagram of operations carried out by the control unit in the device of FIG. 1;

FIGS. 12A and 12B illustrate various output displays in the device of the invention.

DETAILED DESCRIPTION OF THE INVENTION

A. Definitions

Figure 3:
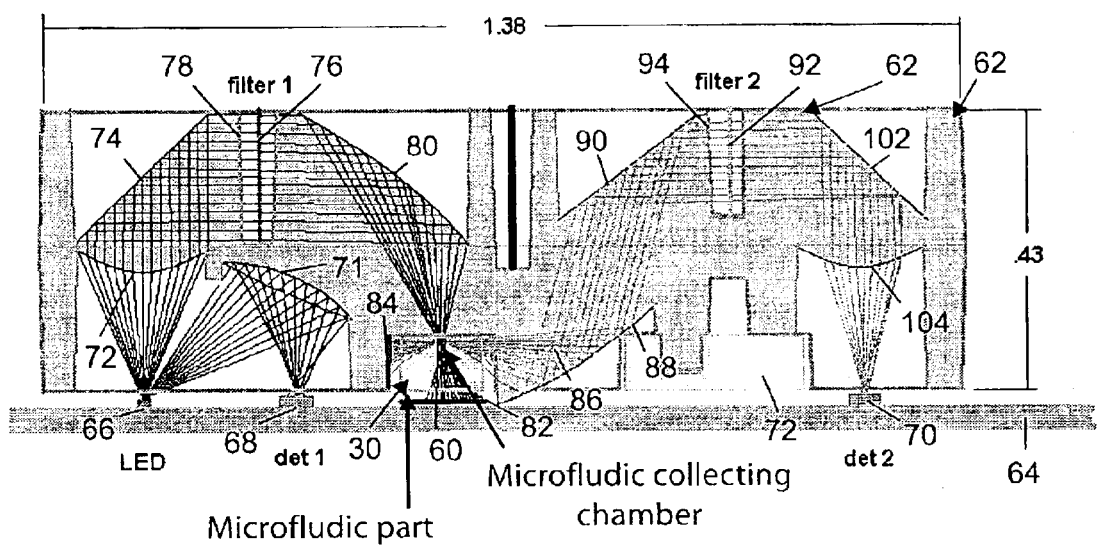
FIG. 3 is a sectional view of an optical element in the assay device of the invention, taken along section line 3—3 in FIGS. 2A and 2C.

The terms below have the following meaning in this application, unless indicated otherwise.

"Microchannel" means a channel having width and depth dimensions that facilitate sperm movement through the channel in a manner similar to the in vivo situation, via the fallopian tube. To count individual forwardly progressing cells, the channel would narrow to limit sperm to single-file movement. Typically the microchannel has width and depth dimensions each between about 10–100 microns. The microchannel may be of any cross-sectioned geometry, such as round or rectangular, and up to many cm in length.

"Labeling compound" refers to any compound that can bind to or incorporate into sperm cells either on their surface or interior, with the result that the sperm cells contains a detectable label, preferably a fluorescent label.

"Motility" refers to the capability of movement, and "sperm motility" specifically to those properties of a sperm cell that allows movement through a fluid medium.

"Forward progression" refers to the capability of sperm to move in a linear fashion.

"Active sperm" refers to those sperm cells which are both motile and forwardly progressing.

"Sperm count" refers to the number of active sperm cell's discriminated and counted by a single detection unit and is related to "sperm concentration" by the volume that count takes place in.

"Sperm density" refers to the density of active sperm cells in the aggregate semen sample and is a measure of male fertility according to the World Health Organization standard of a fertile sample possessing equal to or greater than $20 \times 10^6$ sperm cells/cm$^3$.

B. Assay Device

This section describes the assay device of the invention, illustrating the device with reference to three general embodiments. In the first embodiment, illustrated with reference to FIGS. 1–7 and 12, sperm motility in a forward direction and density of active sperm in a semen sample are determined by sperm migration rate and number from a sample-receiving reservoir through a microfluidic channel of known length into a collection reservoir, where the accumulation of sperm over time is measured. A second embodiment, described with respect to FIGS. 1, 4, 8, 9, and 12 employs a pair of optical detection assemblies at spaced apart positions along a microfluidics channel, for detecting individual sperm as they migrate along the channel between upstream and downstream reservoirs. The third embodiment is illustrate in FIGS. 1 and 10–12, relies on time-dependent changes in electrical impedance in a microfluidics setting to determine sperm motility and density of active sperm.

FIG. 1 illustrates a self-contained device 20 constructed in accordance with the present invention, for measuring sperm motility in a forward direction and density of active sperm in a semen. Shown in this first is an outer case 22 which houses (i) internal microfluidics structure within which sperm motility characteristics will be determined, (ii) a detection system for detecting the movement and/or accumulation of sperm within the microfluidics structure, and (iii) an electronics unit operatively connected to the detection system, for determining sperm characteristics based on detected signals. The construction and operation of these components will be discussed below.

As seen in FIG. 1, the case 22 defines a sample-receiving opening 24 that communicates internally with a sample-receiving reservoir in the microfluidics system in the device, as will be described. Also shown is a cuvette or sample-collection holder 26 for collecting the total ejaculated semen volume, and sample preparation. The cuvette may indicate with a volume-indicator marking (not shown) the minimum semem volume, e.g., the 1.5 mL volume determined necessary by the WHO standards for adequate male fertility. The cuvette may be directly inserted into opening 24 of the device, for transferring fluid from the holder to the microfluidics structure in the device, or an additional sample-preparation vessel may be provided to contain a smaller volume of the total ejaculate semen volume, a dilution of the total sample, or a mixture of the total sample with other liquid or solid chemicals.

The cuvette to be inserted into the sample-receiving well is called the aggregate sample holder and may have a bottom aperture consisting of the entire bottom face of the cuvette, or some smaller geometry set within the bottom face that is readily perforated by a sharpen access (such as a syringe needle) port in the bottom of the opening. The bottom face may be made of rubber or wax to allow perforation without leakage of the sample. The sample may be drawn into the fluidic pathway by capillary action. The sample holder may be pre-loaded or coated with solid and/or liquid chemical compounds, such as a labeling compound and/or digestive enzymes. Digestive enzymes such as collagenase or trypsin may be used to facilitate the natural proteolytic breakdown of the semen sample. Chemicals such as sodium chloride and fructose may be added to increase the in vitro survivability of the semen sample. The cuvette also typically includes a sperm labeling reagent for labeling sperm with a detectable reporter, such as a fluorescent reporter, as discussed below.

The sample holder may be either prefilled with liquid reagents, or these may be supplied to the user in a separate fluid dispenser for addition to the sample in the holder. The liquid reagents may include an iso-osmolar (approximately 290 mOsm) solution of sugar and salt in water, consisting primarily of but not limited to fructose, sodium chloride, calcium chloride, magnesium chloride, and potassium chloride, maintained at physiological pH by HEPES buffering.

The pre-filled solution or solid reagent in the holder may contain a labeling compound, or the labeling compound may be included in solid form in a loading reservoir or in the graduated cylinder. The labeling compound will be weakly fluorescent in solution, either because of concentration or quantum yield, and highly fluorescent on or in the sperm cell, either because of increased concentration due to active accumulation, partition, or esterase activity, or because of increase in quantum yield because of lipid insertion or change in environment.

Once the sample holder is inserted into the device, a sharpened access port is used to pierce the bottom of the aggregate sample holder and the aggregate sample thereby gains access to the fluid pathway within the assay device. Alternatively, the sample, once mixed with the reagents in the cuvette may be poured into the opening, and from there enter the microfluidics structure, e.g., by dissolving an enzyme-dissolvable plug or following removal of a seal by the user.

Also shown in the figure is a display window 28 for displaying assay results to the user. Two exemplary types of display information are discussed below with respect to FIGS. 12A and 12B. Device 20 is manufactured, in a preferred embodiment, as a small, hand-held, disposable device.

C. Device Based on Sperm Detection in a Collection Reservoir

This section describes components of a collection reservoir device constructed in accordance with a first embodiment of the invention. With reference to FIGS. 2A–2F, there is shown at FIG. 2F, a microfluidics structure 30 formed of a bottom plate 32 (FIG. 2A) bonded to an aligned top plate 34 (FIG. 2C) As seen best in FIGS. 2A and 2B, bottom plate 32 includes a tear-drop shaped recess 36 formed in its upper surface, at the upstream end region of the plate, a central cylindrical reservoir recess 38, which will form part of a collection reservoir in the structure, and a downstream recess 40. Also formed in the lower plate is a circular alignment recess 42 used in aligning the lower and upper plates when the two are bonded together, and a tab 44 used in aligning an optical element on structure 30, as will be seen.

Considering now the construction of top plate 34, and with reference to FIGS. 2C–2E, a sample-receiving opening 46 is formed at the upstream end of the plate. A microfluidics channel 48 formed in the lower side of the plate has two separate channel segments: an upstream segment 48a extending from an upstream feed recess 50 to a central reservoir recess 52, and a downstream segment 48 extending recess 52 to a downstream drain recess 54. Recesses 50, 54, and adjoining portions of channel segments 48a, 48b, respectively, are shown in enlarged view in FIG. 2D. Recess 50 (seen in enlarged view in FIG. 2E) has the same circular dimensions as reservoir recess 38 in the bottom plate, and forms therewith, in the assembled structure, a cylindrical collection reservoir 60 (FIG. 2F) in which labeled sperm will collect for detection, as discussed below. In an exemplary embodiment, the collection reservoir has a cylindrical radius of between 0.1 and 1 mm, and a depth of between 0.1 and 1 mm, to produce a known volume of between 0.001 and 1 mm$^3$.

Just downstream of recess 52, in channel segment 48b, is a channel detour 56 (FIG. 2E) which functions to limit flow of motile sperm downstream of the detour, acting thereby to limit the movement of motile sperm beyond the reservoir.

As noted above, the microchannel, in this embodiment, meaning the two microchannel segments 48a, 48b, have width and depth dimensions each between about 10–100 microns, preferably in the range 15–60 microns. The microchannel may be of any cross-sectional geometry, such as semi circular or rectangular, and up to several cms in length. Functionally, the microchannel, and in particularly, microchannel segment 48a, is dimensioned to allow motile sperm to advance through the channel in an upstream to downstream direction, but within a sufficiently confined space that the sperm have a very low probability of reversing their direction of movement within the channel. As will be seen below, the channel width and/or depth may accommodate sperm moving through the channel side by side or may confine the sperm to single-file motion. In the former case, channel width and depth dimensions are preferably between 50 microns and 100 microns; in the latter, between 10 and 30 microns.

As can be appreciated from the forgoing descriptions of plates 32, 34, and from FIG. 2F, the assembled structure has a sample inlet port formed by opening 46, and this port communicates with recess 36 in the lower plate to form a sample-receiving station 47. At its downstream end, recess 36 overlaps with upstream feed recess 50 in the upper plate, for capillary transfer of liquid from recess 36 into recess 50 and from this recess into microchannel 48, where the central region of the microchannel is interrupted by cylindrical collection reservoir 60. From this reservoir, fluid is drawn from the down microchannel 48b to recess 54, which overlaps recess 40, acting to distribute liquid in a drain reservoir formed by recess 40 and opening 40. The fluid pathway just described in structure 30 is typically filled with a suitable liquid medium, e.g., isotonic salt solution, in manufacture, and sealed prior to use. When sample fluid is added to the device, the sample mixes with the preloaded fluid in the sample-receiving station. Sperm contained in the sample, and now in the sample-receiving station, become quickly distributed throughout this station, initiating the series of sperm-migration events which will form the basis for determining sperm motility and density of forward-moving sperm, as described below.

Plates 32, 34 may be fabricated using injection molding of polymer material, preferably transparent polymer such as polypropylene, polycarbonate, or any other optically transparent polymer which is known to provide well-defined and stable molded features. Alternatively, the plates may be formed by well-known surface fabrication methods applied to any of a variety of suitable materials, such as silicon, glass, quartz, plastic, or other polymer. In the latter approach, the channels may be made by laser ablation or chemical etching. Channels of the size proposed can be achieved by focusing the laser used in ablation or by using microlithography to mask the substrate before etching. Each plate has typical width, length, and thickness dimensions of between 0.5 to 2 cm, 2–4 cm, and 1–2 mm. Total thickness of the assembled structure is typically 2–3.5 mm. Recess thickness dimensions, other than for recess 52, are typically 25 to 100 microns.

The two plates, once formed and placed into alignment with one another, are bonded by conventional methods, e.g., chemically, electrostatically, or through heat and pressure (fusion bonding).

With reference to FIG. 3, microfluidics structure 30 is mounted on a plate 64, such as a printed circuit board, which also supports (i) a light-emitting diode 66, which serves as a source of excitation light for fluorescent sample material in the collection reservoir in structure 30, a pair of optical detectors, 68, 70 operable to detect light emission from the sample material in the reservoir, and a unitary optical assembly 62 which has multiple optical elements, as described below, for directing excitation and emission light waves from the LED to the detectors, respectively.

Detection of the emitted light may be accomplished with a photodiode, CCD, or other solid-state detector. These are inexpensive, reliable, have a fast time-response, and available in a wide range of wavelength sensitivity profiles and sizes. An exemplary LED is a UNPRX465-0G1 LED supplied by Uniroyal, which emits light primarily in the blue wavelength around 450–470 nm. An exemplary photodetector is an OSD1-0 photodiode supplied by Centronic.

As can be appreciated from FIGS. 2A and 2C, the optical assembly straddles the center "cut-out" portions of the microfluidics structure, and is aligned therewith by a suitable means between the optical element and tab 44 in structure 30. The optical element is further aligned on plate 64 by interdigitation with a mounting block 72 carried on plate 64.

The various optical elements in the assembly can be understood from a description of their operation in (i) directing a light beam from the LED source onto photodetector 68, to provide a reference for LED light intensity (indicated by black light rays) (ii) focusing an excitation light beam from the LED into the collection reservoir of the microfluidics structure (indicated by black light rays in FIG. 3), and (iii) directing emitted light from the collection reservoir onto photodetector 70, for measuring the level of fluorescence in the reservoir (indicated by gray light rays).

As seen in FIG. 3, divergent light rays from LED 68 are reflected from curved reflecting surface 71 and focused onto detector 71. The light intensity measured at this detector is used to calibrate LED light intensity, relative to light intensity measured at detector 70 resulting from fluorescence emission induced by the LED. Divergent rays from the LED are also directed through a converging lens element 72, producing a light beam with parallel rays, as indicated. These rays are reflected from a right-angle reflecting surface 74, and the reflected beam is passed through a high-pass filter 76 contained in a filter inset 78 in the device. Filter 76 is designed to remove low frequency components produced by the LED, e.g., red and green components that are likely to have overlap with fluorescence emission wavelengths. One preferred filter is a 450–470 nm bandpass filter. The reflected, filtered light is now reflected from a converging reflecting surface 80 which serves to focus the reflected light into collection reservoir 60 in the microfluidics structure. The intensity of excitation light in the sample reservoir is further enhanced by a reflector 82 positioned below the reservoir on plate 64.

As can be appreciated from the ray diagrams in FIG. 3, the above-described optical paths of the excitation light confines the light rays along the directions that are substantially in the vertical direction in the figure. In order to minimize overlap between excitation and emitted light, fluorescence emission is detected from emission rays that are substantially orthogonal to the excitation rays, that is, in a substantially horizontal direction in the figure. This emitted light is either passed directly through an element 86 in the optical assembly or reflected into this element from a reflector 84 located on the opposite side of the collection reservoir. Emitted light directed into element 86 is reflected from a curved reflecting surface 88, from there to an oblique-angle reflector 90, and through a lowpass filter 92 contained in a filter insert 94. The filter is a low-pass filter designed to remove light frequencies above fluorescence emission wavelengths, representing excitation frequencies from the LED. One preferred filter is a 505–540 nm bandpass filter. The filtered emission beam is reflected from right-angle reflecting surface 102, and focused on passing through converging lens element 104 onto detector 70, which then measures intensity of fluorescence emission from sample material in the collection reservoir.

The optical assembly in optical element is formed as a single molded plastic piece, such as molded polyethersulfone, polycarbonate, or acrylic, or other polymer having a relatively high index of refraction and good optical transmission. In the particular embodiment shown, the entire assembly is formed from a single polymer material, although in other embodiment, polymers with different indices of refraction may be employed, e.g., by successively injecting different polymer material into the mold in a controlled injection. The reflecting surfaces on the plate 64 are formed by applying an adhesive tape with a reflective coating. Reflection within the optical component is made by total internal reflection.

The sperm in the sample may be labeled, e.g., fluorescent labeled, by any of a variety of known methods, including attachment of labeled antibodies or selective uptake of a fluorescence label. A preferred embodiment of the later method is illustrated in FIG. 4. The figure shows an individual sperm cell 100 having an outer membrane 102. As is characteristic of mammalian-cell membranes, membrane 102 is more permeable to uncharged molecules than to charged species. The fluorescence labeling agent in the method is a fluorescent molecule having a fluorescence reporter group (F) and a cleavable ester group (—OC(O)—R that can be cleaved at the ester bond by an intracellular esterase into an acidic fluorescent molecule and an alcohol hydrolysis product (R—OH). One preferred fluorescent molecule is Calcein AM ester made by Molecular Probes.

As indicated in the figure, the molecule when esterified exists predominantly in an uncharged form, and as such, can migrate readily into and out of the cell across membrane 102. Once inside the cells, the molecule is subject to modification by an intracellular esterase, cleaving the ester linkage and leaving an acid group that exists largely in a negatively charged form at the intracellular pH. The labeling procedure is carried out preferably in the initial pretreatment of cells, over a labeling period of preferably of at least 5–15 minutes at room temperature. The pretreated sample material added to the microfluidics structure of the device thus includes a suspension of sperm with internalized fluorescent label, and extracellular label in largely uncleaved form.

In another general embodiment, the sperm are detected by light scattering or absorption of light, rather than by fluorescence from a light source, e.g., an LED. For example, the sperm may be labeled with a colored or UV absorbing reporter via an antibody or other sperm-binding agent to which the reporter is derivatized. Alternatively, a colored reporter that becomes cleaved intracellularly, e.g., to form a charged species, may be used in labeling cells. In this embodiment, the optical system described above is modified to detect absorption or light scattering from the cells rather than fluorescence. This may be done, for example, by placing the second photodetector in the optical element directly below (detector 70) the above collection reservoir, such that the accumulation of sperm in the reservoir causes a reduction in light signal at the photodetector.

The dynamics of sperm motility that allows for quantitation of sperm motility and density of active sperm is illustrated in FIGS. 5A–5C. The figures show the microchannel portions of microfluidics structure 30, including the downstream end of feed recess 50, microchannel segment 48a, collection reservoir 60, and microchannel segment 48b. When pretreated semen sample is first introduced into the device, at time t=0, the labeled sperm cells in the sample quickly distribute through the fluid contained in the sample-receiving station. That is, microchannel segment 48a, is virtually free of any labeled cells, as shown in FIG. 5A. Over time, e.g., at time $t=t_1$, motile, forward-moving sperm cells find their way into channel segment 48a, and begin migrating, at a migration rate dependent on the average motility of the cells, toward reservoir 60. As motile, forward-migrating cells complete their journey through channel segment 48a, they begin to accumulate in reservoir 60, leading to an increase in the fluorescence signal measured in the reservoir.

The above cell-migration events, as manifested in fluorescence detection within the reservoir over time are plotted in FIG. 6. At time t=0, measured fluorescence is at some low, background level, and remains so up till time $t_1$, when labeled cells first begin to reach the reservoir. As more and more labeled cells begin to accumulate in the reservoir, the total measured fluorescence begin to rise, in this figure, showing a linear rise over time past $t_1$ with a slope of change in fluorescence/given time period. By extrapolating the slope back to a zero-slope time, $(t_1)$, the time $t_1$ required for migration of sperm cells through channel segment 48b can be determined.

The electronic components of the device include a microprocessor and powered with a small battery. The detector signals are digitized by an AD converter or comparator and then stored in the microprocessor's RAM. The microprocessor then computes the density and motility according to the logic described below. The design and construction of the microprocessor will be evidence to one skilled in the art, given the desired output, and logical operations now to be described.

The steps performed by the device microprocessor, in carrying out these assay determinations, is shown in flow diagram in FIG. 7. When sample is first added to the device, as at box 110, a signal is sent, e.g., by sample fluid closing a conductive pathway between two electrodes, to the microprocessor, setting a clock time to 0, as at 112. Activation may also be done manually through a switch or by connecting a sensor to a foil or plug structure which is covering the sample well. When the protective cover is removed the sample is activated. At the same time LED 66 is switched on, and the microprocessor begins to receive time-dependent fluorescence emission signals from detectors 68 and 70.

Optical detection is continued for a preset time $t_2$ which is long enough to record a reliable plot of increased fluorescence in reservoir 60. When this time is reached, through logic 116, the processor analyzes the fluorescence curve to determine a slope of the time-dependent fluorescence curve, using a standard curve analysis algorithm, as indicated at 118. From this curve, a "zero intercept" where the slope intersects the horizontal baseline is determined, at 120, and from this, the average time of travel of active sperm through channel segment 48a ($t_1-t_0$) and an average velocity of motile sperm are determined at 122, 124, respectively. That is, from the known average time of travel, and the known length of channel segment 48a, the rate of migration of motile cells in a forward direction moving cells within the channel can be calculated (rate=distance/time $t_1$). The calculated velocity, or a qualitative indicator of sperm motility, is displayed to the user at 126.

To determine density of motile sperm, the slope of the time-dependent curve determined at 118 and 120, is compared at 128 with each of a plurality of known slopes, each representing time-dependent fluorescence measurement taken under identical conditions with different known sperm samples, stored at 130. Although not shown in the figure, the slope of the fluorescence curve for sample is adjusted to a standardized excitation intensity to compensate for variations in actual LED excitation intensity, as measured as detector 68 in the device, so that the sample curve and all of the model curves are based on a standardized excitation value. Suitable methods for curve fitting and matching are well known in the art. Once a best curve fit is made, at 132, the density of motile sperm in the sample is estimated from the best-fit curve, and displayed to the user at 126.

The operation of the device, in all three embodiments, is described below, with reference to all three general embodiments of the invention, in Section D below.

D. Device Based on Sperm Detection Along a Microchannel

This section describes components of device constructed in accordance with a second embodiment of the invention, in which sperm motility and density characteristics are measured by a pair of optical detectors positions at spaced apart location along a microfluidics channel. The device is illustrated in particular with respect to FIG. 1, which shows external housing features common to all three embodiments of the invention, FIG. 4, which illustrates fluorescence labeling of sperm cells, shows FIGS. 8A–8C, which illustrate microfluidic channel and optical-sensing components of the embodiment, FIG. 9, showing a flow diagram of the electronically controlled algorithm carried out by the device, and FIG. 12, which illustrates two exemplary output displays that are common to all three embodiments.

Figure 8A:
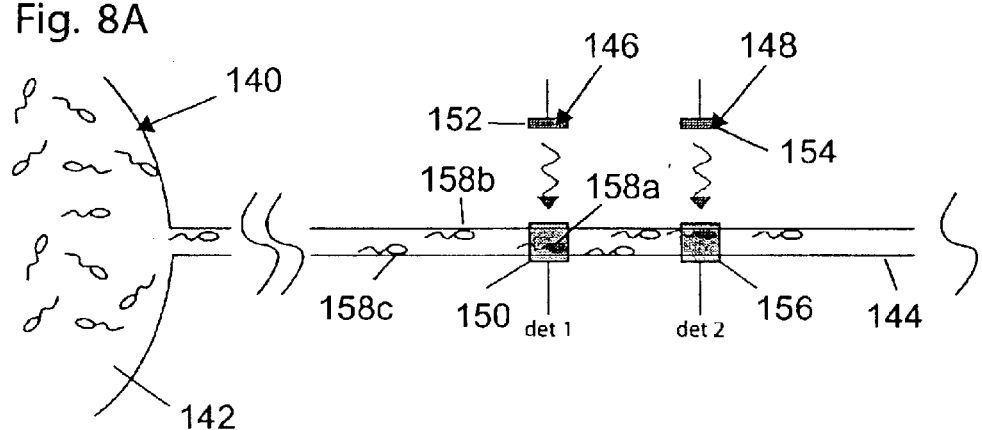
FIGS. 8A–8C show (8A and 8B) plan views of microfluidics structures and associated detectors in a second general embodiment of the invention, and (8C) typical optical detection signals recorded from the two detectors.
Figure 8B:
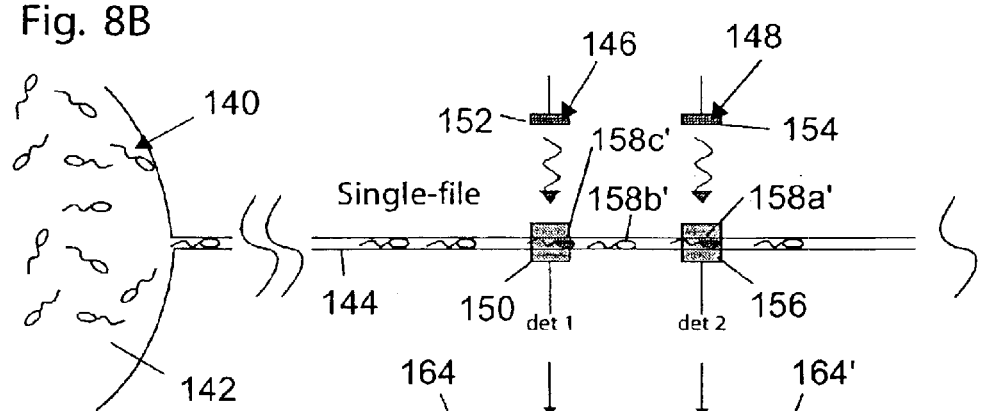
Figure 9:
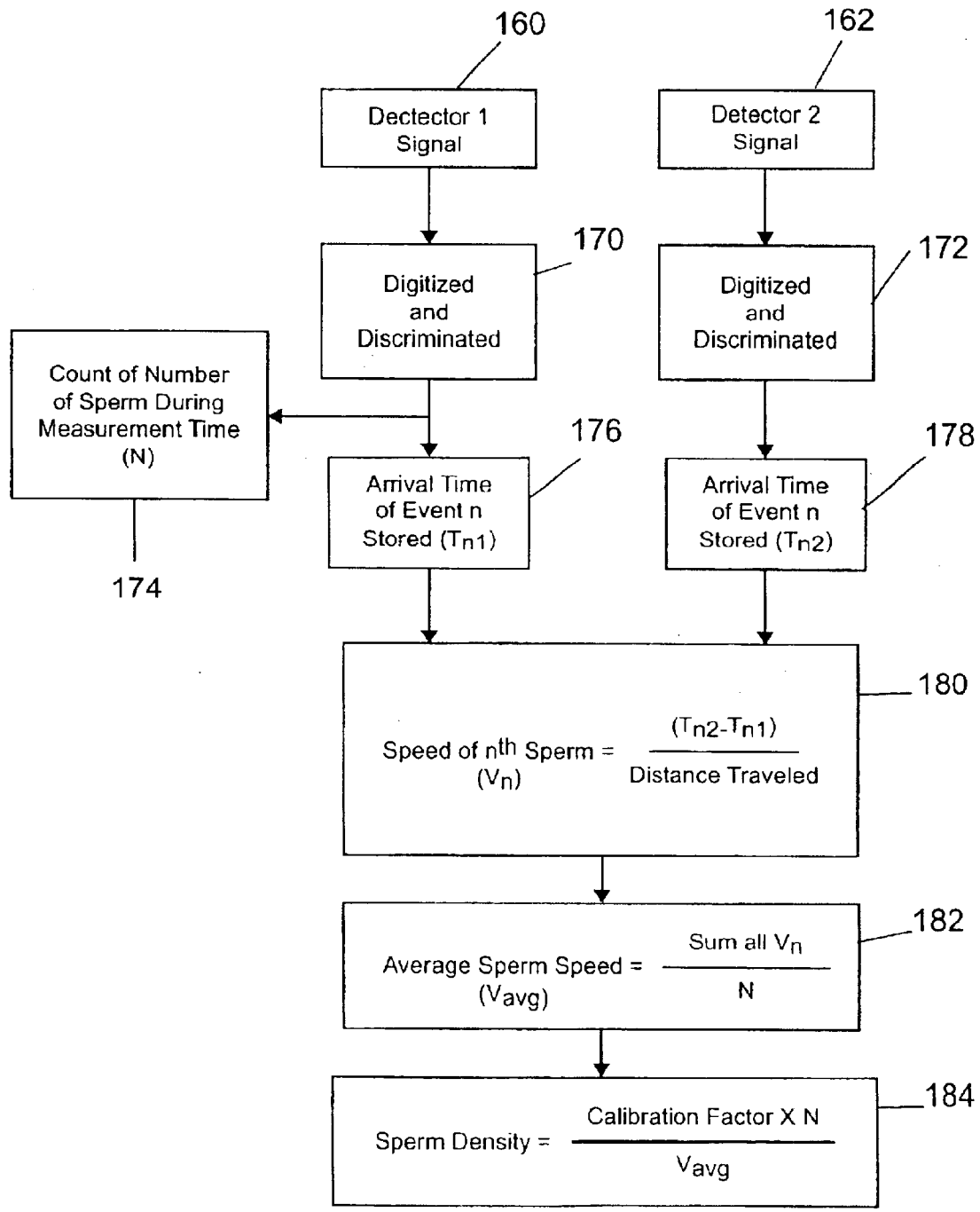
FIG. 9 is a flow diagram of operations carried out by the control unit in two-detector device of FIG. 8.

FIGS. 8A and 8B illustrate a portion of a microfluidics structure 140 in the second-embodiment device. Shown here are a sample-receiving reservoir 142, and an portion of a microchannel 144 whose upstream end is in fluid communication with reservoir 142. The opposite end of the microchannel communicates with an end reservoir, which acts to prevent already counted sperm cells from returning through the detection channel. Several geometries can be used to generate a functionally infinite end reservoir for the collection of sperm cells that have already passed through the detection channel.

Structure 140 may be manufactured using methods similar to those described above in Section B. The microchannel in the structure has width and depth dimensions similar to those described above, to insure sperm movement in the channel in an upstream to downstream direction. The channel length is preferably between 2–5 cm.

Disposed at spaced positions along the microchannel are two optical detection systems 146, 148, each including an LED light source, such as LED 152 and 154, and a photodetector, such as photodetector 150 and 156, respectively. The LEDs and photodetectors are similar to those described for device 20 above, and are operatively connected to a microprocessor (not shown) for (i) microprocessor activation of the LEDs, when an assay procedure is initiated, and (ii) receiving and processing photodetector signals, to generate the desired sperm motility and sperm density information. Both the light source and the detector can be incorporated into the same integrated part. As will be seen below, the signal from a single detector is used to count sperm passing through the channel. Two light source-detector pairs are placed along the microfluidic channel (in the embodiment shown) to keep track of an individual sperm's time of flight over a fixed distance.

The sample shown in the figures is prepared as above. Sample preparation or pretreatment may include cell fluorescence labeling and suspension of cells in an iso-osmolar solution. The pretreated sample is introduced into the device, as above, with initiation of sperm movement into the through the microchannel at an initial time t=0. FIGS. 8A and 8B represent the positions of sperm in the microchannel at two closely related times $t_1$, and $t_{1+d}$ over which a sperm, e.g., sperm 158a, has traveled from one detector zone to the other.

Figure 8C:
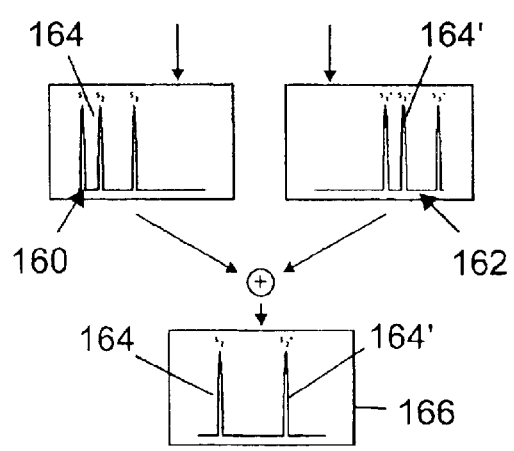

FIG. 8C shows fluorescent signal traces for cells $s_1$, $s_2$, and $s_3$, migrating through channel 144, and taken at the two detection zones at times $t_1$, and $t_2$, corresponding to the cell positions shown in FIGS. 8A and 8B, respectively. In operation, the device processor counts each peak measured at each detector, and assigns that peak a successive new cell number N. Thus, for example, if cell 158a is assigned cell number N detected by detector 150, the same cell should be assigned the same number detected by detector 156. Then, by comparing the time interval between corresponding "same-numbered" cells, the device can determine the time of travel of each sperm "N" between detectors. This is illustrated in FIG. 8C, the bottom frame of which shows at 166, the fluorescent signal peaks detected for corresponding peaks 164 and 164' at the upstream and downstream detectors, respectively.

The migration of sperm through the microchannel may be either single file only, due to the constraining width of the microchannel, or both single and side-by-side pairs. Where more than one cell is passing through a detection zone at the same time, this will be recorded as a multiple-cell event based on the greater width and/or greater height of the fluorescence peak. Where the microchannel width/depth will accommodate will more than one sperm cell in a side-by-side fashion, the microprocessor may contain conventional signal analysis capability for (i) determining from peak height/width the number of cells contributing to a peak, and (ii) assign the peak cell count numbers (e.g., N+1, N+2) corresponding to the determined numbers of sperm cells.

The operation of the microprocessor in the device for determining average sperm motility and density of active sperm in shown in flow diagram in FIG. 9. First, the raw detector signals from each detector, indicated at 160, 162, are passed through a digitizer and then a discriminator, at 170, 172, respectively, in order to determine the times at which the signal magnitude corresponds to passage of a sperm (events). These times are stored for each detector. For example, the time at which the nth sperm passes first and second detector would be denoted $T_{n1}$, $T_{n2}$, respectively, as indicated at 176, 178, respectively. As noted above, where multiple cells pass through a detection zone at any one time, the greater peak height and/or width is recorded as an appropriate number of cells.

A running count of all sperm passing each detector during the measurement time (N) is kept, at 174, providing the basis of density of active sperm in a sample, based on a total number count/time in the microchannel. As above, the actual density of active sperm may be determined by comparing the actual cells/time detected in the sample with each of a plurality of standard cells/time numbers determined for each of a plurality of known-density samples.

Individual sperm velocity is then calculated by taking the difference between the arrival times of a given sperm at the two detectors and dividing this value by the distance between the detectors, as indicated at 180. Many individual sperm velocities are averaged to calculate the average sperm velocity ($V_n$). Sperm density is estimated as the product of N, $V_n$, and a calibration factor, as indicated at 182. The calibration factor can be determined by independently measuring sperm density, and then dividing it by N and $V_n$. Two exemplary displays of the device are shown in FIGS. 12A and 12b, as described above for device 12.

Although the present embodiment has a pair of spaced apart detectors, for detecting sperm positions at two separate time points, it will be appreciated that the device could readily be modified to measure sperm velocity by a single LED and detector pair, where velocity is measured as a function of peak width.

E. Device Based on Sperm Detection by Impedance Measurements

This section describes components of device constructed in accordance with a third of the invention, in which sperm motility and density characteristics are measured by changes in the impedance across or within a microchannel, as sperm migrate through the channel. The device is illustrated in particular with respect to FIG. 1, which shows external housing features common to all three embodiments of the invention, FIG. 10 which illustrates an exemplary channel and electrode configuration in the device, FIGS. 11A and 11B which illustrate, in simplified form, circuit components in the system, and a typical impedance curve obtained during the course of an assay, and FIG. 12, which illustrates two exemplary output displays that are common to all three embodiments.

Figure 10:
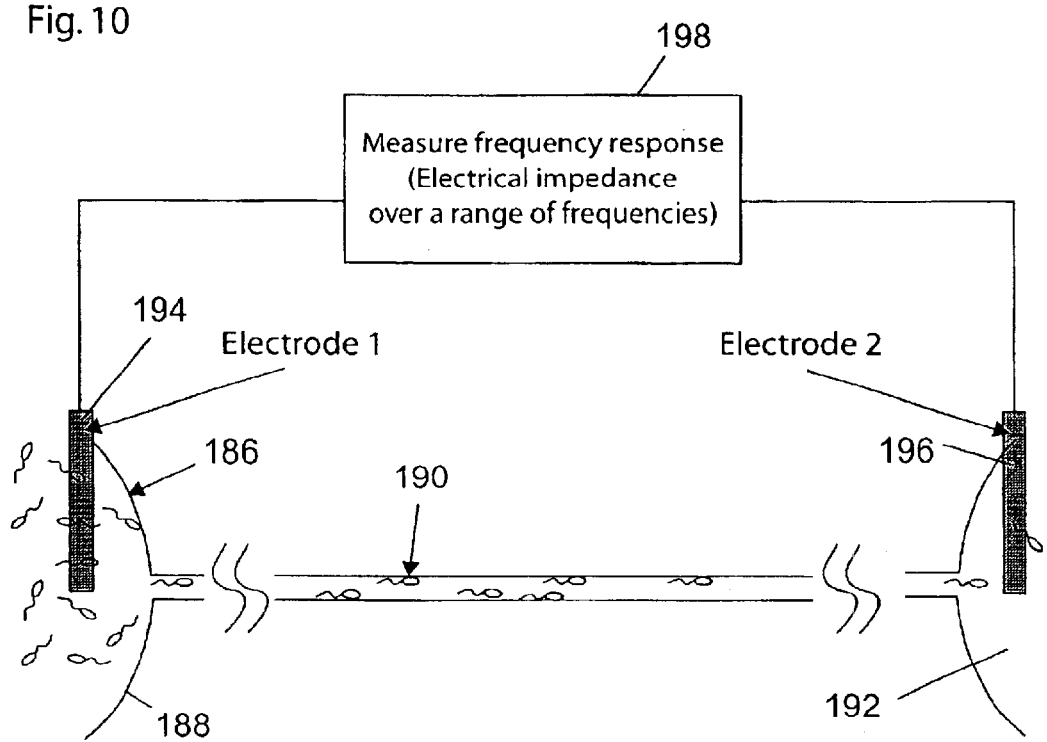
FIG. 10 is a plan view of the microfluidics structure and associated detectors in a third general embodiment of the invention.

FIG. 10 illustrates a portion of a microfluidics structure 186 in the third-embodiment device. Shown here are a sample-receiving reservoir 188, a collection reservoir 192 and a microchannel segment 190 extending there between. Structure 186 may have substantially the same structure as structure 30 described in Section C, and the same manufacture.

A pair of electrodes 194, 196 located within reservoirs 188, 192, respectively, form part of a circuit that includes an electrical excitation unit 198, and the fluid pathway in the microfluidics structure between the two electrodes.

Figure 11A:
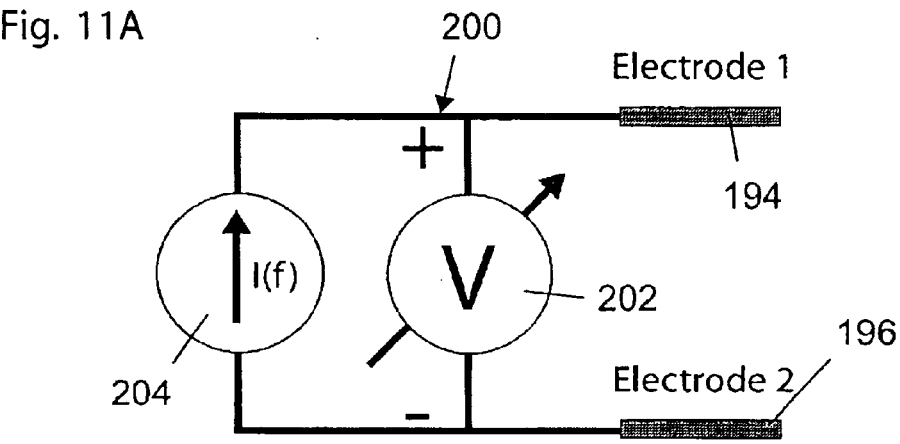
FIGS. 11A and 11B shows an exemplary circuit (11A) and detected signal (11B) in the embodiment of FIG. 10.
Figure 11B:
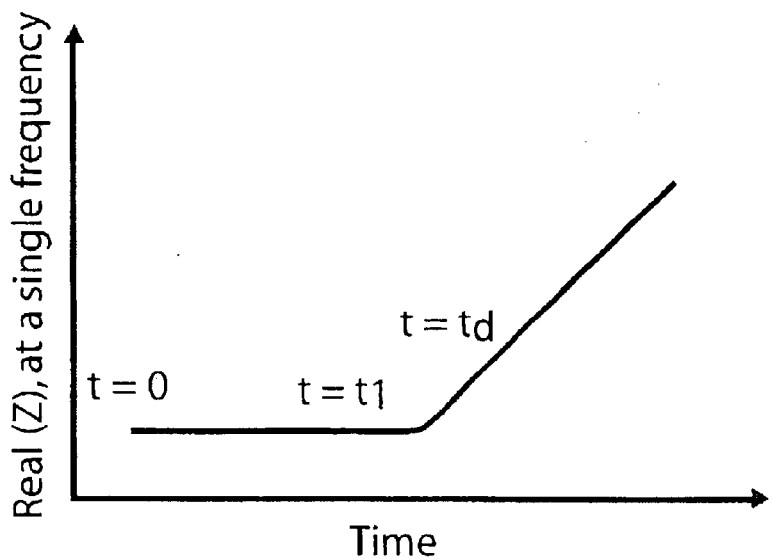

As seen in FIG. 11A, the two electrodes form part of a circuit 200 in the device that includes an AC current source 204 for placing a selected-frequency AC voltage across the electrodes, e.g., at a selected frequency between about 0 and 1 MHz, and a voltmeter 202 measuring voltage in the circuit at any given frequency. The electrical impedance for a given frequency is measured across the electrodes $Z(f)=(V(f)/I(f)$. The real component of the electrical impedance at a given frequency is responsive to the accumulation of sperm in the collection reservoir. Under certain conditions, the real Z(f) will have a time curve like that shown in FIG. 11B, where the measured impedance remains at a substantially constant, baseline level from initialized time t=0 to a time $t_1$, when sperm first begin to enter the collection chamber from the microchannel, and the impedance curve increases with some measured slope as sperm accumulate in the reservoir. The impedance of the reservoir could be periodically scanned through the useful range of frequencies, yielding more information to improve the reliability of the measurement. Note that the impedance could also be measured by using a voltage source and an ammeter.

The impedance curve, it will be recognized, shows the same behavior as the fluorescence curve in FIG. 6, and is processed by the microprocessor in the device in substantially the same way to yield average sperm motility and density of active sperm. In particular, the microprocessor contains a set of impedance curves for sperm samples with known density, for use in curve matching, to determine a best-fit density value. Two exemplary displays of the device are shown in FIGS. 12A and 12b, as described above for device 12.

F. Operation of the Device

This section describes the operation of the device in carrying out a semen-sample analysis, in accordance with the method of the invention, to determine sperm count and motility of a sample.

In a typical sample assay method:

1. Total ejaculate will be collected in a sample collection vial and the volume compared against the WHO standard for male fertility.

2. Either the graduated cylinder or a separate container with a smaller volume or diluted volume or semen mixed with other chemicals, compounds, or solvents is placed into the sample-receiving well of the device. The insertion of the sample holder is locked into place when it is snapped down into the well, the device electronics are activated, and a sharpened access port perforates the bottom of the sample holder giving the internal device fluid channel access to the semen sample. The semen sample flows into a dry loading reservoir or comes into immediate contact with a pre-filled fluid channel. Alternatively, the treated sample could be poured into the sample collection well after the microchannel is unsealed. In the first two embodiments described, sample pretreatment includes labeling the sample sperm with a fluorescence reporter. In the third embodiment, no sample labeling is required.

3. If the prefilled fluid channel is kept separate from a dry loading reservoir, dissolution of a membranous plug by protease activity is initiated with introduction of liquid sample into the reservoir. Alternatively, a seal is removed at to expose the sample to the fluid in the microfluidics channel. Alternatively, a sample vessel is puncture to expose the microfluidics channel to sample fluid.

4. Any of the above events that bring the sample into contact with the microfluidics channel triggers a timing mechanism in the device which sets a timer to t=0, indicating the time at which sperm can first begin to enter and migrate within the microchannel in the device.

5. Sperm migration into and through the microchannel in the device is recorded by (i) fluorescence emission measurement in the collection reservoir in the first embodiment, (ii) measurement of speed and density of individual labeled sperm migration events along the microchannel in the second embodiment, and (iii) measurement of a change in impedance across the microchannel, in the third embodiment.

6. Calculation of WHO criteria is carried out done using a microprocessor, the computer logic of which is shown for the three embodiments in FIGS. 7, 9, and 11.

7. The results, are displayed to the user either in a simple qualitative format, such as shown in FIG. 12A, or in a more quantitative format, such as illustrated in FIG. 12b. In both figures, the display window corresponds to display window 28 in the device, as seen in FIG. 1. The display indicators in FIG. 12A indicate to the user, either continue to wait for the assay to be completed, and, once completed, either a "likely fertile" or "likely infertile" indication, based on measured sperm motility and density of active sperm, using a standard look up table of known sperm motility and density values to classify the sample sperm into one of these two categories.

In the more detailed display in FIG. 12B, actual percentage of motile sperm, relative to normal levels, and actual sperm forward movement rates, relative to normal levels are given.

Although the foregoing invention has been described in detail by way of illustration and example for purposes of clarity of understanding, it will be readily apparent to those of ordinary skill in the art in light of the teachings of this invention that certain changes and modifications may be made thereto without departing from the spirit or scope of the appended claims. In particular, it will be recognized that other embodiments consistent with the claims are contemplated, as are different specific embodiments within each of the three disclosed general embodiment.

For example, it may be desirable to have multiple, independent, fluid filled detection lines originating from the same semen sample. Two or more fluid filled channels may originate in many geometries from the same dry reservoir Independent measurements of this type allow arbitrarily high precision of the sperm cell counting and motility characterization, as each independent measure contributes to the accuracy of the total measurement.

As another example, as modifications on the second embodiment, various electronic or electromagnetic detection systems can be employed to detect the passage of individual sperm along a microchannel, e.g., based on a change in capacitance in a channel portion containing a sperm cell, or based on magnetic effects produced by metal-labeled sperm.

What is claimed is:

1. A device for assaying sperm motility and density of motile sperm in a semen sample comprising a microfluidics structure having a sample reservoir, a downstream collection region and a microchannel extending therebetween, said microchannel being dimensioned to confine sample sperm to single-direction movement within the channel, such that sperm in a semen sample placed in the sample reservoir enter and migrate along said microchannel toward and into said collection region, a detector positioned for detecting the presence of sperm at a detection zone in said microchannel or in a collection region, and an electronics unit operatively connected to said detector for (i) receiving detector signals, (ii) based on the detector signals received, determining information related to sperm motility and density in the sperm sample, and (iii) displaying such information related to sperm motility and density, wherein (a) if the detector is positioned to detect the presence of sperm in said collection region, the electronics units operates to (1) measure the change in concentration of cells present in the collection reservoir as a function of time, (2) determine from step (1), information related to the density of active sperm in said sample, and (3) determine from step (1), information related to the motility of sperm migrating through said micro channel in a forward direction; and (b) if the detector is positioned to detect the presence of sperm at a detection zone in said microchannel, the electronics unit operates to (1) detect individual sperm as they migrate through said zone in the microchannel, in an upstream to downstream direction, (2) count the number of sperm that migrate through the detection zone, and (3) determine the rate of migration of individual sperm through said detection zone.

2. The device of claim 1, wherein said microchannel has width and depth dimensions each in the range of 10–100 $\mu$m.

3. The device of claim 1, wherein the detector is positioned to detect the presence of sperm in said collection region and said electronics unit operates, in carrying out step (1) to generate a time-dependent function whose slope approximates the change in number of cells present in the collection reservoir per unit of time, and whose intercept approximates the time to first appearance of sperm in said collection reservoir, in carrying out step (2) to compare said function with one or more standard functions generated with semen samples of different known sperm counts and rates of forward progression, and in carrying out step (3) to determine from said intercept, the average rate of travel in a forward direction of said sperm.

4. The device of claim 1, wherein the detector is positioned to detect the presence of sperm in said collection region and said detector includes an LED, first and second photodetectors, and an optical member designed to (1) direct light from the LED to the first photodetector, (2) direct light from the LED through the collection reservoir, and (3) direct emitted fluorescence from the collection reservoir capture to the second photodetector.

5. The device of claim 4, wherein said optical member is a unitary member composed of a plurality of optical elements having different indices of refractions.

6. The device of claim 1, wherein the detector is positioned to detect the presence of sperm at a detection zone in said microchannel and the width of said microchannel is between about 15–40 µm.

7. The device of claim 1, wherein the detector is positioned to detect the presence of sperm at a detection zone in said microchannel and said detection zone is defined by a pair of adjacent, axially spaced detectors, and said electronics unit operates, in carrying out step (1) to correlate detection signals received from each detector to enhance the signal-to-noise ratio for each detection event.

8. The device of claim 1, wherein the detector is positioned to detect the presence of sperm at a detection zone in said microchannel and said detection zone is defined by a pair of adjacent, axially spaced detectors, and said electronics unit operates, in carrying out step (3), to use the time interval between signals received from said detectors to determine the rate of migration of sperm within the microchannel.

9. The device of claim 1, wherein the detector is positioned to detect the presence of sperm at a detection zone in said micro channel and said detector includes a fluorescence excitation light source, and a fluorescence emission detector.

10. The device of claim 1, wherein the detector is positioned to detect the presence of sperm at a detection zone in said microchannel and said detector includes a circuit element disposed adjacent said detection zone, said circuit element being responsive to nearby movement of magnetic- or metal-conductor particles, such that movement of sperm labeled with magnetic or metal-conductor particles through said detection zone in the microchannel will alter the inductance of said element, and said electronics unit includes a detector circuit operatively coupled to said element for detecting changes in the inductance of said element.

11. The device of claim 10, wherein said electronics unit operates, in carrying out step (3), to determine the rate of migration of a sperm passing through said detection zone from the rate of change of signal characteristics generated by the circuit element.

12. The device of claim 1, wherein the detector is positioned to detect the presence of sperm in said microchannel and said electronics unit operates, in carrying out step (2), to count the number of sperm passing through a detection zone over a known time period, and find a comparable sperm count/time value on a standard curve generated with semen samples of different known sperm counts.

13. The device of claim 1, wherein said sample-receiving reservoir communicates with the upstream end of said microchannel through a degradable, liquid-impervious plug, and said reservoir contains an enzyme capable of degrading said plug.

14. The device of claim 1, which is formed as a self-contained unit with its own power supply for powering the electronics unit and detector.

* * * * *